United States Patent
Squiquera et al.

(10) Patent No.: US 10,293,032 B2
(45) Date of Patent: May 21, 2019

(54) METHODS AND PHARMACEUTICALS FOR TREATMENT OF VIRAL INFECTIONS OF THE EYE

(71) Applicant: Tamir Biotechnology, Inc., San Diego, CA (US)

(72) Inventors: Luis Squiquera, Buenos Aires (AR); Jamie Sulley, Old Saybrook, CT (US)

(73) Assignee: TAMIR BIOTECHNOLOGY, INC., Short Hills, NJ (US)

( * ) Notice: Subject to any disclaimer, the term of this patent is extended or adjusted under 35 U.S.C. 154(b) by 43 days.

(21) Appl. No.: 15/180,270

(22) Filed: Jun. 13, 2016

(65) Prior Publication Data

US 2016/0361392 A1 Dec. 15, 2016

Related U.S. Application Data

(60) Provisional application No. 62/175,961, filed on Jun. 15, 2015.

(51) Int. Cl.
| | |
|---|---|
| *A61K 9/08* | (2006.01) |
| *A61K 38/46* | (2006.01) |
| *A61K 9/00* | (2006.01) |
| *A61K 47/02* | (2006.01) |

(52) U.S. Cl.
CPC .......... *A61K 38/465* (2013.01); *A61K 9/0048* (2013.01); *A61K 9/08* (2013.01); *A61K 47/02* (2013.01); *C12Y 301/27* (2013.01); *Y02A 50/382* (2018.01); *Y02A 50/385* (2018.01); *Y02A 50/393* (2018.01)

(58) Field of Classification Search
None
See application file for complete search history.

(56) References Cited

U.S. PATENT DOCUMENTS

| | | | |
|---|---|---|---|
| 4,882,421 A | 11/1989 | Shogen et al. | |
| 5,559,212 A | 9/1996 | Ardelt | |
| 5,728,805 A | 3/1998 | Ardelt | |
| 5,955,073 A | 9/1999 | Rybak et al. | |
| 6,175,003 B1 | 1/2001 | Saxena | |
| 6,239,257 B1 | 5/2001 | Ardelt | |
| 6,423,515 B1 | 7/2002 | Saxena | |
| 7,229,824 B2 | 6/2007 | Saxena | |
| 7,442,535 B2 | 10/2008 | Saxena | |
| 7,442,536 B2 | 10/2008 | Saxena | |
| 7,473,542 B2 | 1/2009 | Saxena | |
| 7,556,951 B2 | 7/2009 | Saxena | |
| 7,556,952 B2 | 7/2009 | Saxena | |
| 7,556,953 B2 | 7/2009 | Saxena | |
| 7,572,882 B2 | 8/2009 | Sette et al. | |
| 7,585,654 B2 | 9/2009 | Saxena | |
| 7,585,655 B2 | 9/2009 | Saxena | |
| 7,763,449 B2 | 7/2010 | Saxena | |
| 8,518,399 B2 | 8/2013 | Saxena et al. | |
| 8,663,964 B2 | 3/2014 | Saxena et al. | |
| 8,808,690 B2 | 8/2014 | Saxena et al. | |
| 9,642,794 B2 | 5/2017 | Sulley et al. | |
| 2003/0099629 A1 | 5/2003 | Goldenberg et al. | |
| 2004/0072910 A1 | 4/2004 | Porat | |
| 2005/0014161 A1 | 1/2005 | Saxena | |
| 2007/0231890 A1 | 10/2007 | Saxena | |
| 2007/0231891 A1 | 10/2007 | Saxena | |
| 2007/0232543 A1 | 10/2007 | Saxena | |
| 2007/0232544 A1 | 10/2007 | Saxena | |
| 2007/0238861 A1 | 10/2007 | Saxena | |
| 2007/0243605 A1 | 10/2007 | Saxena | |
| 2007/0243606 A1 | 10/2007 | Saxena | |
| 2008/0033151 A1 | 2/2008 | Saxena | |
| 2008/0161324 A1 | 7/2008 | Johansen et al. | |
| 2009/0081759 A1 | 3/2009 | Saxena | |
| 2009/0081776 A1 | 3/2009 | Saxena | |
| 2009/0081777 A1 | 3/2009 | Saxena | |
| 2009/0081778 A1 | 3/2009 | Saxena | |
| 2009/0099348 A1 | 4/2009 | Saxena | |
| 2009/0111175 A1 | 4/2009 | Saxena | |
| 2009/0202513 A1 | 8/2009 | Ramon-nino et al. | |
| 2009/0246214 A1 | 10/2009 | Goldenberg et al. | |
| 2010/0291657 A1 | 11/2010 | Saxena | |
| 2010/0304463 A1 | 12/2010 | Saxena | |
| 2010/0317082 A1 | 12/2010 | Saxena | |
| 2011/0274704 A1 | 11/2011 | Chang et al. | |

(Continued)

FOREIGN PATENT DOCUMENTS

| | | |
|---|---|---|
| WO | WO 1996/039428 A1 | 12/1996 |
| WO | WO 1997/031116 A2 | 8/1997 |

(Continued)

OTHER PUBLICATIONS

Langston ("Herpes Simplex Virus in the Eye", Digital Journal of Ophthalmology, Oct. 2002) (Year: 2002).*
PCT/US1999/030799, International Search Report and Written Opinion dated May 30, 2000, 7 pages.
PCT/US2000/023426, International Search Report dated Nov. 27, 2000, 3 pages.
PCT/US2004/014844, International Search Report and Written Opinion, dated May 10, 2006, 8 pages.
PCT/US2004/014844, International Preliminary Report on Patentability, dated Feb. 15, 2007, 5 pages.
PCT/US2015/022670, International Search Report and Written Opinion, dated Nov. 18, 2015, 29 pages.

(Continued)

*Primary Examiner* — Louise W Humphrey
*Assistant Examiner* — Charles Zoltan Constantine
(74) *Attorney, Agent, or Firm* — Cooley LLP

(57) ABSTRACT

Viral infections of the eye, and particularly viral infections in the Herpesviridae and Adenoviridae families, can be treated by administration of a pharmaceutical made up of an enzymatically active ribonuclease and a vehicle. Advantageously, the enzymatically active ribonuclease is ranpirnase, the '805 variant, rAmphinase 2, and Amphinase 2, and the vehicle is an aqueous solution.

18 Claims, 4 Drawing Sheets

Specification includes a Sequence Listing.

(56) References Cited

U.S. PATENT DOCUMENTS

| | | | |
|---|---|---|---|
| 2012/0121569 A1* | 5/2012 | Saxena | A61K 38/465 424/94.6 |
| 2012/0149085 A1 | 6/2012 | Goldenberg et al. | |
| 2012/0260922 A1 | 10/2012 | Gómez-acebo et al. | |
| 2013/0022589 A1 | 1/2013 | Saxena et al. | |
| 2014/0030246 A1 | 1/2014 | Saxena et al. | |
| 2014/0037610 A1 | 2/2014 | Saxena et al. | |
| 2014/0128396 A1 | 5/2014 | Schadt et al. | |
| 2015/0010524 A1 | 1/2015 | Jain | |
| 2015/0376584 A1 | 12/2015 | Hodge | |
| 2016/0045431 A1 | 2/2016 | Sulley et al. | |
| 2016/0045574 A1 | 2/2016 | Sulley et al. | |
| 2017/0157219 A1 | 6/2017 | Hodge | |
| 2017/0296647 A1 | 10/2017 | Sulley et al. | |

FOREIGN PATENT DOCUMENTS

| | | | |
|---|---|---|---|
| WO | WO 1997/038112 A1 | 10/1997 | |
| WO | WO 2000/040608 A1 | 7/2000 | |
| WO | WO 2001/018214 A1 | 3/2001 | |
| WO | WO 2004/061120 A2 | 7/2004 | |
| WO | WO 2005/017100 A2 | 2/2005 | |
| WO | WO 2005/080586 A1 | 9/2005 | |
| WO | 2013/039857 A1 | 3/2013 | |
| WO | WO-2013089835 A1 * | 6/2013 | ........... A61K 9/0048 |
| WO | WO 2016/028634 A1 | 8/2015 | |
| WO | WO 2015/148768 A2 | 10/2015 | |
| WO | WO 2016/205109 A1 | 12/2016 | |
| WO | WO 2017/142807 A1 | 8/2017 | |

OTHER PUBLICATIONS

PCT/US2015/022670, International Preliminary Report on Patentability, dated Oct. 4, 2016, 21 pages.
PCT/US2015/045272, International Search Report and Written Opinion, dated Dec. 1, 2015, 9 pages.
PCT/US2015/045272, International Preliminary Report on Patentability, dated Feb. 21, 2017, 6 pages.
PCT/US2016/037174, International Search Report and Written Opinion, dated Oct. 12, 2016, 14 pages.
"Anti Viral Status in Quarterly Report for Tamir Biotechnology." Alfacell Corporation, ACEL—InvestorVillage, published Aug. 15, 2011 [retrieved on Feb. 8, 2017]. Retrieved from the internet, 2 pages. <URL: http://www.investorvillage.com/mbthread.asp?mb=470&tid =10843482&showall =1>.
"Tamir Reports Positive Effect Against SARS Virus." Tamir Biotechnology, Inc., published on Oct. 21, 2010 [retrieved on Feb. 8, 2017]. Retrieved from the internet, 2 pages. <URL:http://globenewswire.com/news-release/2010/07/21/425595/197044/en/Tamir-Reports-Positive-Effect-Against-SARS-Virus.html>.
"Tamir's Compounds Show Remarkable Results Against Dengue Virus", Tamir Biotechnology, Inc., published Jul. 19, 2010 [retrieved on Feb. 8, 2017]. Retrieved from the internet, 3 pages. <URL: http://www.globenewswire.com/news-release/2010/07/19/425341/196757/en/Tamir-s-Compounds-Show-Remarkable-Results-Against-Dengue-Virus.html>.
Adinolfi, B.S., et al., "Full antitumor action of recombinant seminal ribonuclease depends on the removal of its N-terminal methionine." Biochem Biophys Res Commun. (1995); 213(2): 525-532.
Anonymous: "Baltimore classification—Wikipedia, the free encyclopedia", published Mar. 6, 2013 [retrieved on Feb. 13, 2013]. Retrieved from the internet, 5 pages. <URL:https://en.wikipedia.org/w/index.php?title=Baltimore_classification&oldid=542396320>.
Ardelt, W., et al., "Amino acid sequence of an anti-tumor protein from Rana pipiens oocytes and early embryos. Homology to pancreatic ribonucleases." J Biol Chem. (1991); 266(1): 245-251.
Ardelt, W., et al., "Onconase and Amphinase, the Antitumor Ribonucleases from Rana pipiens Oocytes." Curr Pharm Biotechnol. (2008); 9(3): 215-225.

Baltimore, D., "Expression of Animal Virus Genomes", Bacteriological Reviews (1971); 35(3): 235-241.
Boix, E., et al., "Role of the N terminus in RNase A homologues: differences in catalytic activity, ribonuclease inhibitor interaction and cytotoxicity." J Mol Biol. (1996); 257(5): 992-1007.
Branden et al., Introduction to Protein Structure, Garland Publishing Inc., New York, p. 247, 1991, 24 pages.
Bucher, M.H., et al., "Differential effects of short affinity tags on the crystallization of Pyrococcus furiosus maltodextrin-binding protein." Acta Crystallogr D Biol Crystallogr. (2002);58(Pt 3): 392-397. Epub Feb. 21, 2002.
Chao, Q., et al., "Expression and partial characterization of Dolichos biflorus seed lectin in Escherichia coli." Arch Biochem Biophys. (1994); 313(2): 346-350.
Chaudhuri, T.K., et al., "Effect of the extra n-terminal methionine residue on the stability and folding of recombinant α-lactalbumin expressed in Escherichia coli." J Mol Biol. (1999); 285(3): 1179-1194.
Chen, C-Y., et al., "Cloning, sequencing and expression of a cDNA encoding bovine pancreatic deoxyribonuclease I in Escherichia coli: purification and characterization of the recombinant enzyme." Gene (1998); 206(2): 181-184.
Domachowske, J.B. et al., "Eosinophil cationic protein/RNase 3 is another RNase A-family ribonuclease with direct antiviral activity", Nucleic Acids Research (1998); 26(14): 3358-3363.
Durmazlar, K., et al., "Cantharidin treatment for recalcitrant facial flat warts: a preliminary study." J. Dermatol. Treatment (2009); 20(2): 114-119.
Dyer and Rosenberg, "The RNase a superfamily: generation of diversity and innate host defense." Mol Divers. (2006); 10(4): 585-597.
Fonda, I., et al., "Attachment of histidine tags to recombinant tumor necrosis factor-alpha drastically changes its properties." ScientificWorldJournal (2002); 2: 1312-1325.
Geurrero, S.A., et al., "His-tagged tryparedoxin peroxidase of Trypanosoma cruzi as a tool for drug screening." Appl Microbiol Biotechnol. (2000); 53(4): 410-414.
Goda, S., et al., "Effect of extra N-terminal residues on the stability and folding of human lysozyme expressed in Pichia pastoris." Protein Engineering (2000); 13(4): 299-307.
Gupta, P.K., et al., "Role of N-Terminal Amino Acids in the Potency of Anthrax Lethal Factor." PLoS ONE (2008); 3(9): e3130.
Hariri, S., et al., "Human Papillomavirus." Centers for Disease Control VPD Surveillance Manual, 5th edition, Chapter 5, pp. 1-11 (2011).
Hirel, P.H., et al., "Extent of N-terminal methionine excision from Escherichia coli proteins is governed by the side-chain length of the penultimate amino acid." PNAS USA (1989); 86(21): 8247-8251.
Ho, S.N., et al., "Site-directed mutagenesis by overlap extension using the polymerase chain reaction." Gene (1989); 77(1): 51-59.
Huang, H-C., et al., "The Rana catesbeiana rcr Gene Encoding a Cytotoxic Ribonuclease. Tissue Distribution, Cloning, Purification, Cytotoxicity, and Active Residues for RNase Activity." J. Biol. Chem. (1998); 273(11): 6395-6401.
Ishikiwa, N., et al., "Remarkable destabilization of recombinant alpha-lactalbumin by an extraneous N-terminal methionyl residue." Protein Eng. (1998); 11(5): 333-335.
Kamiya, Y., et al., "Amino acid sequence of a lectin from Japanese frog (Rana japonica) eggs." J Biochem. (1990); 108(1): 139-143.
Lehninger, A.L. (1975) Biochemistry, Second Edition, p. 962, 5 pages.
Liao, Y.D., et al., "Removal of N-terminal methionine from recombinant proteins by engineered E. coli methionine aminopeptidase." Protein Sci. (2004); 13(7): 1802-1810.
Lin, J-J. et al., "Characterization of the mechanism of cellular and cell free protein synthesis inhibition by an anti-tumor ribonuclease", Biochemical and Biophysical Research Communications (1994); 204(1): 156-162.
Moore, J.A., et al., "Equivalent Potency and Pharmacokinetics of Recombinant Human Growth Hormones with or without an N-Terminal Methionine." Endocrinology (1988); 122(6): 2920-2926.

(56) References Cited

OTHER PUBLICATIONS

Moreau, J.M. et al., "Diminished expression of an antiviral ribonuclease in response to pneumovirus infection in vivo" Antiviral Research (2003); 59(3): 181-191 (Abstract).

Mosimann, S.C., et al., "Comparative molecular modeling and crystallization of P-30 protein: A novel antitumor protein of Rana pipiens oocytes and early embryos." Proteins (1992); 14(3): 392-400.

Notomista, E., et al., "Effective expression and purification of recombinant onconase, an antitumor protein." FEBS Letters (1999); 463(3): 211-215.

Park, K.S., et al., "Biologic and biochemic properties of recombinant platelet factor 4 demonstrate identity with the native protein." Blood (1990); 75: 1290-1295.

Porta, C., et al., "Ranpirnase and its potential for the treatment of unresectable malignant mesothelioma." Biologics (2008); 2(4): 601-609.

Qiao, M. et al., "Onconase downregulates microRNA expression through targeting microRNA precursors", Cell Research (2012); 22(7): 1199-1202.

Saxena, S.K., et al., "Effect of Onconase on Double-stranded RNA In Vitro." Anticancer Research (2009); 29(4): 1067-1072.

Saxena, S.K., et al., "Onconase® and its Therapeutic Potential." Lab Medicine (2003); 34(5): 380-387.

Seffernick, J.L., et al., "Melamine Deaminase and Atrazine Chlorohydrolase: 98 Percent Identical but Functionally Different." Journal of Bacteriology (2001); 183(8): 2405-2410.

Studier, F.W., et al., "Use of T7 RNA polymerase to direct expression of cloned genes." Methods Enzymol. (1990); 185: 60-89.

Suhasini and Sirdeshmukh, "Transfer RNA cleavages by onconase reveal unusual cleavage sites." J Biol Chem. (2006); 281(18): 12201-12209. Epub Feb. 23, 2006.

Supplementary European Search Report in European application No. EP 04751988.9, completed May 30, 2007 and dated Jun. 6, 2007, 6 pages.

Suzuki, M., et al., "Engineering receptor-mediated cytotoxicity into human ribonucleases by steric blockade of inhibitor interaction." Nat Biotechnol. (1999); 17(3): 265-270.

Takano, K., et al., "Effect of foreign N-terminal residues on the conformational stability of human lysozyme." The FEBS Journal (1999); 266(2): 675-682.

Trimble and Frazer, "Development of therapeutic HPV vaccines." Lancet Oncol. (2009); 10(10): 975-980.

UniProtKB—Amphinase-2 entry (2007), 5 pages.

Witkowski, A., et al., "Conversion of a β-Ketoacyl Synthase to a Malonyl Decarboxylase by Replacement of the Active-Site Cysteine with Glutamine." Biochemistry, (1999); 38(36): 11643-11650.

Wu and Filutowicz, "Hexahistidine ($His_6$)-tag dependent protein dimerization: a cautionary tale." Acta Biochim Pol. (1999); 46(3): 591-599.

Wu, Y., et al., "A cytotoxic ribonuclease. Study of the mechanism of onconase cytotoxicity." The Journal of Biological Chemistry (1993); 268(14): 10686-10693.

Turcotte et al: "Design and Characterization of an HIV-Specific Ribonuclease Zymogen", AIDS Research and Human Retroviruses, vol. 24, No. 11 (Nov. 1, 2008), pp. 1357-1363. p. 1357, left column, last paragraph p. 1358, right column, paragraph 2; p. 1362, left column, last paragraph.

Saxena et al: "Inhibition of HIV-1 Production and Selective Degradation of Viral RNA by an Amphibian Ribonuclease", Journal of Biological Chemistry, vol. 271, No. 34 (Aug. 23, 1996), pp. 20783-20788. Abstract, Figures 1-4.

Ilinskaya et al: "Ribonucleases as antiviral agents", Molecular Biology Acadamy of Sciences of the USSR, vol. 48, No. 5 (Oct. 11, 2014), pp. 615-623. Abstract, p. 617, right column, paragraph 2-p. 618, left column, paragraph 3.

PCT/US2016/037174, International Preliminary Report on Patentability, dated Dec. 19, 2017, 9 pages.

PCT/US2017/043984, International Search Report and Written Opinion, dated Oct. 10, 2017, 15 pages.

\* cited by examiner

Scale for Scoring Ocular Lesions

| CORNEA |
|---|
| A. Opacity - Degree of Density (area most dense taken for reading) |
| No ulceration or opacity ............................................................................................................ 0 |
| Scattered or diffuse areas of opacity (other than slight dulling of normal luster), details of iris clearly visible ............................................................................................... **1 |
| Easily discernible translucent areas, details of iris slightly obscured ........................................... 2 |
| Opalescent areas, no details of iris visible, size of pupil barely discernible ................................ 3 |
| Opaque, iris invisible ................................................................................................................. 4 |
| B. Area of Cornea Involved |
| One quarter (or less), but not zero ............................................................................................ 1 |
| Greater than one quarter, but less than half ............................................................................. 2 |
| Greater than half, but less than three quarters ......................................................................... 3 |
| Greater than three quarter, up to whole area ............................................................................ 4 |
| Score = A x B x 5                                                                         Total Maximum = 80 |
| IRIS |
| A. Values |
| Normal ....................................................................................................................................... 0 |
| Markedly deepened rugae, congestion, swelling, moderate circumcorneal hyperemia or injection, or any combinations thereof; iris still reacting to light (sluggish reaction is positive) ......................... **1 |
| No reaction to light, hemorrhage, gross destruction (any or all of these) ................................... 2 |
| Score = A x 5                                                                              Total Maximum = 10 |
| CONJUNCTIVAE |
| A. Redness (refers to palpebral and bulbar conjunctivae excluding cornea and iris) |
| Vessels Normal .......................................................................................................................... 0 |
| Vessels definitely injected above normal .................................................................................. 1 |
| More diffuse, deeper crimson red, individual vessels not easily discernible ............................ **2 |
| Diffuse beefy red ....................................................................................................................... 3 |
| B. Chemosis |
| No swelling ................................................................................................................................ 0 |
| Any swelling above normal (includes nictitating membrane) .................................................... 1 |
| Obvious swelling with partial eversion of lids ........................................................................... **2 |
| Swelling with lids about half closed ........................................................................................... 3 |
| Swelling with lids about half closed to completely closed ......................................................... 4 |
| C. Discharge |
| No discharge ............................................................................................................................. 0 |
| Any amount different from normal (does not include small amounts observed in inner canthus of normal animals) ............................................................................ 1 |
| Discharge with moistening of the lids and hairs just adjacent to lids ....................................... 2 |
| Discharge with moistening of the lids and hairs and considerable area around the eyes ....... 3 |
| Score = (A + B + C) x 2                                                                Total Maximum = 20 |
| Cornea + Iris + Conjunctivae Scores                             Total Maximum Score Possible = 110 |

**Figures indicate lowest grades considered positive under the U.S. Health Effects Test Guideline (1998), OPPTS 870.2400

FIGURE 1

Ocular Observations/Post Treatment - Test Article Treated

| Animal #/Sex | | Pre-Dose | 1 Hour | 24 Hour | 48 Hour | 72 Hour |
|---|---|---|---|---|---|---|
| 2671 Male | Cornea | | | | | |
| | A. Opacity-Degree | 0 | 0 | 0 | 0 | 0 |
| | B. Area Involved | 0 | 0 | 0 | 0 | 0 |
| | A x B x 5 = | 0 | 0 | 0 | 0 | 0 |
| | Iris | | | | | |
| | A. Values | 0 | 0 | 0 | 0 | 0 |
| | A x 5 = | 0 | 0 | 0 | 0 | 0 |
| | Conjunctivae | | | | | |
| | A. Redness | 0 | 1 | 0 | 0 | 0 |
| | B. Chemosis | 0 | 1 | 0 | 0 | 0 |
| | C. Discharge | 0 | 1 | 0 | 0 | 0 |
| | (A + B + C) x 2 = | 0 | 6 | 0 | 0 | 0 |
| | TOTAL SCORE | 0 | 6 | 0 | 0 | 0 |
| Animal #/Sex | | Pre-Dose | 1 Hour | 24 Hour | 48 Hour | 72 Hour |
| 2672 Male | Cornea | | | | | |
| | A. Opacity-Degree | 0 | 0 | 0 | 0 | 0 |
| | B. Area Involved | 0 | 0 | 0 | 0 | 0 |
| | A x B x 5 = | 0 | 0 | 0 | 0 | 0 |
| | Iris | | | | | |
| | A. Values | 0 | 0 | 0 | 0 | 0 |
| | A x 5 = | 0 | 0 | 0 | 0 | 0 |
| | Conjunctivae | | | | | |
| | A. Redness | 0 | 1 | 0 | 0 | 0 |
| | B. Chemosis | 0 | 0 | 0 | 0 | 0 |
| | C. Discharge | 0 | 1 | 0 | 0 | 0 |
| | (A + B + C) x 2 = | 0 | 4 | 0 | 0 | 0 |
| | TOTAL SCORE | 0 | 4 | 0 | 0 | 0 |
| Animal #/Sex | | Pre-Dose | 1 Hour | 24 Hour | 48 Hour | 72 Hour |
| 2673 Male | Cornea | | | | | |
| | A. Opacity-Degree | 0 | 0 | 0 | 0 | 0 |
| | B. Area Involved | 0 | 0 | 0 | 0 | 0 |
| | A x B x 5 = | 0 | 0 | 0 | 0 | 0 |
| | Iris | | | | | |
| | A. Values | 0 | 0 | 0 | 0 | 0 |
| | A x 5 = | 0 | 0 | 0 | 0 | 0 |
| | Conjunctivae | | | | | |
| | A. Redness | 0 | 1 | 0 | 0 | 0 |
| | B. Chemosis | 0 | 0 | 0 | 0 | 0 |
| | C. Discharge | 0 | 1 | 0 | 0 | 0 |
| | (A + B + C) x 2 = | 0 | 4 | 0 | 0 | 0 |
| | TOTAL SCORE | 0 | 4 | 0 | 0 | 0 |

FIGURE 2

Ocular Observations/Post Treatment - Untreated

| Animal #/Sex | | Pre-Dose | 1 Hour | 24 Hour | 48 Hour | 72 Hour |
|---|---|---|---|---|---|---|
| 2671 Male | Cornea | | | | | |
| | A. Opacity-Degree | 0 | 0 | 0 | 0 | 0 |
| | B. Area Involved | 0 | 0 | 0 | 0 | 0 |
| | A x B x 5 = | 0 | 0 | 0 | 0 | 0 |
| | Iris | | | | | |
| | A. Values | 0 | 0 | 0 | 0 | 0 |
| | A x 5 = | 0 | 0 | 0 | 0 | 0 |
| | Conjunctivae | | | | | |
| | A. Redness | 0 | 0 | 0 | 0 | 0 |
| | B. Chemosis | 0 | 0 | 0 | 0 | 0 |
| | C. Discharge | 0 | 0 | 0 | 0 | 0 |
| | (A + B + C) x 2 = | 0 | 0 | 0 | 0 | 0 |
| | TOTAL SCORE | 0 | 0 | 0 | 0 | 0 |
| Animal #/Sex | | Pre-Dose | 1 Hour | 24 Hour | 48 Hour | 72 Hour |
| 2672 Male | Cornea | | | | | |
| | A. Opacity-Degree | 0 | 0 | 0 | 0 | 0 |
| | B. Area Involved | 0 | 0 | 0 | 0 | 0 |
| | A x B x 5 = | 0 | 0 | 0 | 0 | 0 |
| | Iris | | | | | |
| | A. Values | 0 | 0 | 0 | 0 | 0 |
| | A x 5 = | 0 | 0 | 0 | 0 | 0 |
| | Conjunctivae | | | | | |
| | A. Redness | 0 | 0 | 0 | 0 | 0 |
| | B. Chemosis | 0 | 0 | 0 | 0 | 0 |
| | C. Discharge | 0 | 0 | 0 | 0 | 0 |
| | (A + B + C) x 2 = | 0 | 0 | 0 | 0 | 0 |
| | TOTAL SCORE | 0 | 0 | 0 | 0 | 0 |
| Animal #/Sex | | Pre-Dose | 1 Hour | 24 Hour | 48 Hour | 72 Hour |
| 2673 Male | Cornea | | | | | |
| | A. Opacity-Degree | 0 | 0 | 0 | 0 | 0 |
| | B. Area Involved | 0 | 0 | 0 | 0 | 0 |
| | A x B x 5 = | 0 | 0 | 0 | 0 | 0 |
| | Iris | | | | | |
| | A. Values | 0 | 0 | 0 | 0 | 0 |
| | A x 5 = | 0 | 0 | 0 | 0 | 0 |
| | Conjunctivae | | | | | |
| | A. Redness | 0 | 0 | 0 | 0 | 0 |
| | B. Chemosis | 0 | 0 | 0 | 0 | 0 |
| | C. Discharge | 0 | 0 | 0 | 0 | 0 |
| | (A + B + C) x 2 = | 0 | 0 | 0 | 0 | 0 |
| | TOTAL SCORE | 0 | 0 | 0 | 0 | 0 |

FIGURE 3

EEC Ocular Evaluation Criteria

| Scoring Parameter | EEC Risk Phrase | Mean Ocular Irritation Score (6 animals) or Individual Mean Ocular Irritation Scores in 2/3 animals (3 animals) | Irritation Rating |
|---|---|---|---|
| Corneal Opacity | - | 0.00 - 1.99 | Nonirritant |
|  | Irritating to eyes | 2.00 - 2.99 | Irritant |
|  | Risk of serious damage to eyes | ≥3.00 | Serious Damage |
| Iris Lesion | - | 0.00 - 0.99 | Nonirritant |
|  | Irritating to eyes | 1.00 - 1.99* | Irritant |
|  | Risk of serious damage to eyes | ≥2.00** | Serious Damage |
| Conjunctival Redness | - | 0.00 - 2.49 | Nonirritant |
|  | Irritating to eyes | ≥2.50 | Irritant |
| Conjunctival Edema | - | 0.00 - 1.99 | Nonirritant |
|  | Irritating to eyes | ≥2.00 | Irritant |

\* 1.5 for 6 animals rather than 1.99 for 3 animals.
\*\* >1.50 for 6 animals rather than ≥ 2.00 for 3 animals.

FIGURE 4

ABSTRACT

METHODS AND PHARMACEUTICALS FOR TREATMENT OF VIRAL INFECTIONS OF THE EYE

BACKGROUND OF THE INVENTION

The invention relates to viral infections of the eye, and more particularly relates to methods and pharmaceuticals for treatment of viral infections of the eve. In its most immediate sense, the invention relates to treatment of human eye infections caused by Herpesviridae viruses (including but not limited to Human cytomegalovirus, herpes zoster virus, and varicella zoster virus) and Adenoviridae viruses.

Viral diseases of the eye can have significant consequences. Type 1 herpes simplex virus can cause conjunctivitis and keratitis, Human cytomegalovirus can cause retinitis, adenovirus types 8, 19, 29, and 37 can cause epidemic keratoconjunctivitis, and adenovirus types 3, 4, and 7 can cause pharyngoconjuctival fever. Herpes zoster virus (HZV), a member of the Herpesviridae family, can cause severe eye disease when affecting the trigeminal area. Herpes zoster ophthalmicus, a severe form of acute herpes zoster, results from the reactivation of varicella zoster virus (VZV) (another member of the Herpesviridae family) in the trigeminal (fifth cranial) nerve. Any branch of the nerve may be affected, though the frontal branch within the first division of the trigeminal nerve is most commonly involved. This frontal branch innervates nearly all of the ocular and periocular structures. Herpes zoster ophthalmicus at this particular location can lead to blindness and requires a fast and effective therapeutic approach.

Human cytomegalovirus (CMV) is another member of the Herpesviridae family. At least 60% of the US population has been exposed to CMV, with a prevalence of more than 90% in high- risk groups (e.g., unborn babies whose mothers become infected with CMV during pregnancy, people with HIV, and transplant recipients).

CMV retinitis is one of the most common opportunistic infections in persons with AIDS or pharmacologically induced immunosuppression. Individuals with CMV retinitis typically exhibit a progressive decrease in visual acuity, which may progress to blindness. Long-term CMV treatment is necessary to prevent retinitis relapse.

Immune reconstitution syndrome (IRIS) is reported in 16-63% of HIV-infected patients with CMV retinitis following the initiation of HAART (Highly Active Antiretroviral Treatment). CMV IRIS may manifest as painless floaters, blurred vision, photopia, decreased visual acuity, or ocular pain. Some Patients may develop macular edema leading to vision loss or proliferative vitreoretinopathy, spontaneous vitreal hemorrhage, and retinal detachment.

It is known to treat viral eye infections with acyclovir but such treatment is not entirely satisfactory. Topical acyclovir must be applied frequently and causes irritation of the eye. Oral acyclovir causes significant adverse side effects. Other antiviral medications such as gancyclovir, valacyclovir and valgancyclovir are used to treat viral eye infections, and such treatments are also not entirely satisfactory. Gancyclovir is administered intravenously, and therefore cannot be used outside e.g. a hospital setting. Oral antiviral medications such as valacyclovir and valgancyclovir have disadvantages; they are known to cause fever, rash, diarrhea, and hematologic effects (e.g., neutropenia, anemia, thrombocytopenia). In some cases neutropenia may respond to lowering the dose or using drugs that stimulate the production of neutrophils by the bone marrow as granulocyte colony-stimulating factor [G-CSF], or granulocyte-macrophage colony-stimulating factor [GM-CSF]. These toxic effects can be difficult to manage.

It would therefore be advantageous to provide a better method and a better pharmaceutical for treating viral eye infections in humans.

Various enzymatically active ribonucleases, including ranpirnase and other proteins that are highly homologous to it, are known to have antiviral activity, and to have activity against viruses in the Herpesviridae family (specifically including but not limited to Herpes simplex virus types 1 and 2 and Human cytomegalovirus) and also against type 2 adenovirus. However, proteins are known to be highly irritating to the eye due to an intense inflammatory response mediated by T-cells. For this reason, although ranpirnase and other related proteins have been investigated for use against various viral infections, they have not been investigated for use against viral infections of the eye.

Despite the expectation that proteinaceous ranpirnase would cause irritation in the eye, irritation of topically applied ranpirnase in the eye was studied in a rabbit model. In this experiment, ranpirnase was demonstrated to be non-irritating as determined using the Globally Harmonized System of Classification Evaluation Criteria and the European Economic Community Ocular Evaluation Criteria. This was a remarkable result, because administration of a foreign protein to the eye can produce corneal irritation. As a result, ranpirnase and other proteins that are highly homologous to it are expected to be useful in treating viral infections of the human eye.

BRIEF DESCRIPTION OF THE DRAWINGS

The invention will be better understood with reference to the following exemplary and non-limiting drawings, in which:

FIG. 1 shows the scale used for scoring ocular lesions observed in a rabbit that has undergone a Draize test;

FIG. 2 shows the results of a Draize test in which a ranpirnase solution was applied to the right eye of three rabbits;

FIG. 3 shows the results of the Draize test of FIG. 2 in which the left eye of each of the rabbits was untreated; and FIG. 4 shows the European Economic Community Ocular Evaluation Criteria used to classify the ocular irritation caused by a test article in a Draize test.

DETAILED DESCRIPTION OF PREFERRED EMBODIMENTS

Ranpirnase is a proteinaceous enzymatically active ribonuclease (the word "ribonuclease" is frequently abbreviated as "RNase") that is disclosed and claimed in U.S. Pat. No. 5,559,212. U.S. Pat. Nos. 5,728,805, 6,239,257, 7,229,824 and U.S. Pat. No. 8,518,399 disclose three other proteinaceous enzymatically active ribonucleases that are highly homologous to ranpirnase:

a) the ribonuclease of SEQ ID NO:2 in U.S. Pat. No. 5,728,805, herein referred to as: the "'805 variant";

b) the ribonuclease of SEQ ID NO:2 in U.S. Pat. No. 6,239,257, herein referred to as "Amphinase 2", and;

c) the ribonuclease of SEQ ID NO:59 of U.S. Pat. No. 7,229,824, herein referred to as "rAmphinase 2".

U.S. Pat. No. 8,518,399 discloses that ranpirnase, the '805 variant, and rAmphinase 2 have antiviral activity against Herpesviridae viruses, specifically including but not limited to Herpes simplex types 1 and 2 and Human cytomegalovirus. Based upon its similarities with these three enzymatically active ribonucleases, it is believed that Amphinase 2 will have these activities as well.

Commonly-owned copending patent application Ser. No. 14/736,170 filed Jun. 10, 2015 and published as US 2015/0376584 A1 discloses that ranpirnase has antiviral activity against a number of viruses, including type 2 adenovirus. As stated therein, the viruses in the Adenoviridae family are very closely related and the demonstrated antiviral activity of ranpirnase against any one virus within the Adenoviridae family is strong evidence that ranpirnase will have the same anti-replication activity against all viruses within the Adenoviridae family. Furthermore, as stated in that pending patent application, to a person of ordinary skill in this art, the similarities of homology and activity of these three other ribonucleases is strong evidence that these three other ribonucleases will have the same activity as ranpirnase has. Hence, although in vitro experiments have not yet been repeated using the '805 variant, Amphinase 2, or rAmphinase 2, a person of ordinary skill in this art would conclude that these three ribonucleases will likewise be active against all the viruses in the Adenoviridae family.

Thus, ranpirnase, the '805 variant, Amphinase 2, and rAmphinase 2 have either been demonstrated to be active against type 1 Herpes simplex virus and viruses in the Adenoviridae family or would be expected to be so active. For this reason, a person of ordinary skill in the art would expect that all four of these proteinaceous enzymatically active ribonucleases will be useful against viral infections of the human eye.

All four of these ribonucleases are members of the ribonuclease A superfamily. Such ribonucleases are pyrimidine-specific endonucleases found in high quantity in the pancreas of certain mammals and of some reptiles. They are involved in endonucleolytic cleavage of 3'-phosphomononucleotides and 3'-phosphooligonucleotides ending in C-P or U-P with 2',3'-cyclic phosphate intermediates. Other members of this superfamily include bovine seminal vesicle and brain ribonucleases, kidney non-secretory ribonucleases, liver-type ribonucleases, angiogenin; eosinophil cationic protein, pancreatic ribonucleases from different species including human, and bovine pancreatic ribonucleases.

Ranpirnase, which is disclosed in U.S. Pat. No. 5,559,212, and was previously known by the ONCONASE trademark, is a ribonuclease isolated from oocytes of the leopard frog Rana pipiens. The amino acid sequence of ranpirnase is provided in SEQ ID NO: 1. Ranpirnase has been tested and found to be cytotoxic to cancer cells because of its enzymatic activity against RNA.

A variant of ranpirnase (hereinafter, the "'805 variant") is disclosed in U.S. Pat. No. 5,728,805. The '805 variant is also a ribonuclease, and has likewise been found to be cytotoxic to certain cancer cells. The '805 variant is a close variant of ranpirnase; its amino acid sequence is identical to that of ranpirnase except that it has valine instead of isoleucine at position 11, asparagine instead of aspartic acid at position 20, and arginine instead of serine at position 103 of the ranpirnase amino acid sequence. The '805 variant has been referred to as "Valli, Asn20, Arg103-Ranpirnase". The amino acid sequence of the '805 variant is provided in SEQ ID NO:2.

Amphinase 2 is also a ribonuclease. It is the protein identified as 2325p4 in U.S. Pat. No. 6,239,257 and it too has been found to be cytotoxic to cancer cells. The amino acid sequence of Amphinase 2 is provided in SEQ ID NO: 3.

Recombinant Amphinase 2 ("rAmphinase 2") is similar to Amphinase 2, but has a Net residue at position −1 and lacks glycan moieties that are located in Amphinase 2 at positions 27 and 91. rAmphinase 2 is described in U.S. Pat. No. 7,229,824. The amino acid sequence of rAmphinase 2 is provided in SEQ ID NO: 4.

The term "functional equivalent" is intended to mean any protein that differs from any naturally occurring ribonuclease by the deletion, addition or substitution of one or more amino acids, but that retains ribonuclease activity. For example, the '805 variant is a functional equivalent of ranpirnase, because it comprises three amino acid substitutions compared to the ranpirnase amino acid sequence, but still has RNase activity.

The disclosures of U.S. Pat. Nos. 5,559,212, 5,728,805, 6,239,257, 7,229,824, 8,518,399, 8,663,964 and published patent application US 2015/0376584 A1 are all incorporated by reference herein in their entireties for all purposes.

As discussed above, it has been found that a ribonuclease of the RNase A superfamily, in particular ranpirnase, can be used in the treatment of a viral infection of the eye. A "viral infection of the eye" is a disease which shows symptoms predominantly in the eye of a subject and which is caused by viruses rather than bacteria. Viral diseases of the eye include, but are not limited to, conjunctivitis and keratitis, retinitis, keratoconjunctivitis, chorioretinitis, pharyngoconjuctival fever and CMV retinitis.

Viral conjunctivitis, also known as pink eye, is characterized by inflammation of the outermost layer of the white part of the eye and the inner surface of the eyelid. Viral conjunctivitis is typically caused by an adenovirus. Other viruses that can be responsible for conjunctival infection include herpes simplex virus (HSV), varicella-zoster virus (VZV), enterovirus 70, Coxsackie virus A24, molluscum contagiosum and human immunodeficiency virus (HIV).

Viral keratitis is an inflammation of the cornea which is predominantly caused by herpes simplex virus.

Chorioretinitis is an inflammation of the choroid (thin pigmented vascular coat of the eye) and retina of the eye. It is a form of posterior uveitis. Chorioretinitis can be caused by infection with cytomegalovirus (CMV), Varicella-Zoster (HZV), dengue fever, West Nile virus or lymphocytic choriomeningitis virus (LCMV).

In particular, viral infections of the eye can be caused by a virus from the Herpesviridae family of viruses and by an adenovirus selected from the group consisting of 3, 4, 7, 8, 19, 29, and 37. Herpesviridae are viruses having a double-stranded, linear DNA genome which are classified in Baltimore class I. Viruses from the Herpesviridae family causing viral infections of the eye include, but are not limited to, type I Herpes simplex virus, human cytomegalovirus and Herpes zoster virus, in particular Herpes zoster ophthalmicus.

Adenoviridae are double-stranded DNA viruses which are classified in Baltimore class I. Adenovirus types 8, 19, 29, and 37 can cause epidemic keratoconjunctivitis, and adenovirus types 3, 4, and 7 can cause pharyngoconjuctival fever types 8, 19, 29, and 37 can cause epidemic keratoconjunctivitis, and Adenovirus types 3, 4, and 7 can cause pharyngoconjuctival fever.

The terms "treating" and "treatment," as used herein, refer to administering to a subject having a viral infection of the eye a therapeutically effective dose of a ribonuclease such as ranpirnase, a ranpirnase variant such as the '805 variant, Amphinase 2, or rAmphinase 2. As used herein, the term "treating" covers any treatment of a viral infection of the eye which results in a desired pharmacologic and/or physiologic effect, including arresting disease development, causing regression of the disease, limiting spread of the virus from one cell to another within an individual, limiting replication of a virus in an individual, limiting entry of a virus into the cell of an individual and reducing the number of viruses in an individual or a tissue of this individual.

The term "therapeutically effective dose" refers to an amount of a pharmaceutical that results in an improvement or remediation of the symptoms of a disease or condition to be treated. A therapeutically effective dose of a ribonuclease such as ranpirnase, '805 variant, Amphinase 2, or rAmphinase 2, delays or minimizes the onset of, or hastens or increases recovery of a subject from, a viral infection of the eye in a subject. The RNase may reduce the viral titer in the eye of the infected subject, or may prevent the viral titer in the eye of the infected subject from increasing. A therapeutically effective dose of a ribonuclease may provide a therapeutic benefit in the treatment or management of a viral infection of the eye by reducing the spread of the virus from one cell to another and may also prevent disease and/or reduce the severity of symptoms.

A therapeutically effective dose can be determined by the skilled person as a matter of routine experimentation. The therapeutically effective dosage of the pharmaceutical composition can be determined readily by the skilled artisan, for example, from animal studies. In addition, human clinical studies can be performed to determine the preferred effective dose for humans by a skilled artisan. Such clinical studies are routine and well known in the art. The precise dose to be employed will also depend on the route of administration. Effective doses may be extrapolated from dose-response curves derived from in vitro or animal test systems.

The RNase may be administered to a subject in need thereof in a single dose or in multiple doses. The RNase may be administered to the subject until symptoms resolve and/or until the subject is no longer at risk of a virus infection. The schedule on which the administration of the RNase (advantageously, ranpirnase) commences, and on which a single dose or multiple doses of the RNase (advantageously, ranpirnase) is or are administered to the subject, and the duration of dosing, can be determined by a person of ordinary skill. These factors may depend on factors such as the severity of symptoms, patient response, etc.

The administration of a therapeutically effective dose of the RNase (advantageously, ranpirnase) may reduce the virus titer in the eye compared to a control that is infected with the virus but not treated with the RNase.

The administration of a therapeutically effective dose of the RNase (advantageously, ranpirnase) may lead to a reduction of the virus titer below the detection level. Determination of virus titers is for example discussed in Reischl (1996) Front Biosci. 1:e 72-7, Application of molecular biology-based methods to the diagnosis of infectious diseases.

The ribonuclease (advantageously, ranpirnase) is preferably administered topically to the eye, i.e. is administered directly to the eye and not elsewhere on the body. The topical administration may be by e.g. eye drops, a suspension, an emulsion, an ointment, a solution, a gel, liposomes, nanoparticles, microemulsions, nanoemulsions, nanosuspensions, niosomes, dendrimers and hydrogels. Alternatively, the ribonuclease (advantageously, ranpirnase) may be administered by the intravitreal, intracameral, subconjunctival, subtenon, retrobulbar or posterior juxtascleral route.

The ribonuclease will be a component of a pharmaceutical that includes a vehicle. The term "vehicle" includes any and all solvents, dispersion media, coatings, antibacterial and antifungal agents, isotonic and absorption delaying agents and the like. The use of such media and agents for pharmaceutically active substances is well known in the art. These agents are generally safe, non-toxic and neither biologically nor otherwise undesirable.

The vehicle may contain ingredients such as an excipient, a surfactant, an ingredient to adjust the pH of the composition and to buffer within a certain pH range, and a tonicity agent to adjust the tonicity of the composition. Such ingredients are known, and persons of ordinary skill in the art can select such of them as will produce a formulation having appropriate characteristics when combined with the RNase (advantageously, ranpirnase).

It is possible to determine whether a substance (here, a ribonuclease) is non-irritating to the eye in a Draize test using the Globally Harmonized System of Classification Evaluation Criteria and using the European Economic Community Ocular Evaluation Criteria. In the Draize test the RNase is placed in the conjunctival sac of a rabbit's eye and the eye is examined at 1, 24, 48 and 72 hours after instillation of ranpirnase. The criteria evaluated are corneal opacity, iris lesion, conjunctival redness and conjunctival edema. If the score for each of these criteria is zero, the tested substance is considered non-irritating to the eye. FIGS. 1 and 4 show, respectively, the scale used for scoring ocular lesions observed in a rabbit that has undergone a Draize test and the European Economic Community Ocular Evaluation Criteria used to classify the ocular irritation caused by a test article in a Draize test.

As stated above, before the present invention, no person of ordinary skill in the art would administer to the eye ranpirnase or any of the other three above-identified proteinaceous enzymatically active ribonucleases. However, such administration of ranpirnase has been modeled using the Draize test and the results of this experiment demonstrate that ranpirnase is non-irritating as defined by two accepted standards.

EXAMPLE

A 0.1% mL solution made up of 0.1% ranpirnase in a proprietary aqueous solution used as a vehicle was used as a test article. Three rabbits were used; each was a male New Zealand White rabbit that was approximately 16 weeks old at the time of the experiment and that weighed 3.3 to 3.4 kg.

After administration of two drops of Tetracaine pre-anesthetic to the corneal surface of both eyes of each rabbit, the test article was placed in the conjunctival sac of the right eye of each rabbit by gently pulling the lower lid away from the eyeball; the lids were gently held together for approximately one second to limit the loss of the test material. The left eye of each rabbit remained untreated and served as the control. The eyes of the animals were examined at 1 (±15 minutes), 24, 48, and 72 hours (±1 hour) after installation of the test article. The grades of ocular reaction according to Draize (FIG. 1) were manually recorded at each examination (FIGS. 2 and 3). As can be seen in FIG. 2, there was an ocular reaction in each animal one hour post-instillation of the test article but in every instance that reaction was completely resolved by 24 hours and thereafter.

To determine the degree of irritation caused by the test article using the European Economic Community Ocular Evaluation Criteria (FIG. 4), the total ocular irritation scores for the examinations at 24, 48, and 72 hours were individually added for corneal opacity, iris lesion, conjunctival redness, and conjunctival edema and the mean scores for these scoring parameters were compared to the European Economic Community Ocular Evaluation Criteria. Because all these scores (and therefore the calculated mean scores) were zero, the test subject was considered to be non-irritating as defined by the European Economic Community Ocular Evaluation Criteria.

To determine the degree of irritation caused by the test article using the Globally Harmonized System of Classification Evaluation Criteria, the 24-, 48-, and 72-hour scores were added separately for each animal and each total divided by 3 (three time points) to yield the individual mean scores for each animal. Because all these scores (and therefore the calculated quotients) were zero, the test subject was considered to be non-irritating as defined by the Globally Harmonized System of Classification Evaluation Criteria.

Hence, these test data demonstrate a new and unexpected result: ranpirnase delivered to the eye in an aqueous solution is non-irritating as defined by the Globally Harmonized System of Classification Evaluation Criteria and by the European Economic Community Ocular Evaluation Criteria, even though ranpirnase is a protein (which would be expected to be irritating to the eye).

Although this experiment was carried out using a solution of ranpirnase in a proprietary aqueous vehicle, a person of ordinary skill in the art would consider it likely that solutions of the three above-identified proteinaceous enzymatically active ribonucleases would behave in the same way because of their similarities to ranpirnase in respect of activity and homology.

Although at least one preferred embodiment of the invention has been described above, this description is not limiting and is only exemplary. The scope of the invention is defined only by the claims, which follow:

The invention claimed is:

1. A method of treating an adenoviral infection of the eye, comprising the step of administering to the eye a therapeutically effective dose of a ribonuclease that is a member of the ribonuclease A superfamily.

2. The method of claim 1, wherein the eye is a human eye and the ribonuclease is selected from a group consisting of a. ranpirnase;
b. the '805 variant;
c. Amphinase 2; and
d. rAmphinase 2.

3. The method of claim 1, wherein the ribonuclease is non-irritating to the eye as determined using a. the Globally Harmonized System of Classification Evaluation Criteria and
b. the European Economic Community Ocular Evaluation Criteria.

4. The method of claim 1, wherein the eye is a human eye and the ribonuclease is functionally equivalent to a ribonuclease selected from a group consisting of:
a. ranpirnase;
b. the '805 variant;
c. Amphinase 2; and
d. rAmphinase 2.

5. A method for treating an adenoviral infection of the human eye, the method comprising administering an ophthalmic composition to the eye, the composition comprising:
a. a therapeutically effective dose of a ribonuclease that is a member of the ribonuclease A superfamily and that is non-irritating to the eye as determined using
i. the Globally Harmonized System of Classification Evaluation Criteria and
ii. the European Economic Community Ocular Evaluation Criteria; and
b. a vehicle.

6. The method of claim 5, wherein the ribonuclease is selected from a group consisting of:
a. ranpirnase;
b. the '805 variant;
c. Amphinase 2; and
d. rAmphinase 2.

7. The method of claim 5, wherein the vehicle is an aqueous solution.

8. The method of claim 5, wherein the ribonuclease is the functional equivalent of a ribonuclease selected from a group consisting of
a. ranpirnase;
b. the '805 variant;
c. Amphinase 2; and
d. rAmphinase 2.

9. A method of treating an adenoviral infection of an eye, the method comprising the step of topically administering to the eye a therapeutically effective amount of a ranpirnase.

10. The method according to claim 9, wherein the ranpirnase is a recombinant ranpirnase.

11. The method according to claim 9, wherein the ranpirnase is SEQ ID NO: 1 or SEQ ID NO: 2.

12. The method according to claim 9, wherein the adenoviral infection is the cause of viral conjunctivitis, epidemic keratoconjunctivitis, or pharyngoconjuctival fever.

13. The method according to claim 9, wherein the adenoviral infection is caused by an adenovirus 3, an adenovirus 4, an adenovirus 7, an adenovirus 8, an adenovirus 19, an adenovirus 29 or an adenovirus 37.

14. The method according to claim 9, wherein the ranpirnase is formulated as an ophthalmic pharmaceutical composition.

15. The method according to claim 14, wherein the ophthalmic pharmaceutical composition is a solution, a suspension, a nanosuspension, an emulsion, a microemulsion, a nanoemulsion, an ointment, a gel, a hydrogel, liposomes, niosomes, nanoparticles, or dendrimers.

16. The method according to claim 15, wherein the ophthalmic pharmaceutical composition further comprises a pharmaceutically acceptable carrier and/or a pharmaceutically acceptable excipient.

17. The method according to claim 9, wherein the ranpirnase is administered as eye drops.

18. The method according to claim 9, wherein the eye is from a human.

* * * * *

```
                        SEQUENCE LISTING

<160> NUMBER OF SEQ ID NOS: 4

<210> SEQ ID NO 1
   <211> LENGTH: 104
   <212> TYPE: PRT
   <213> ORGANISM: Rana pipiens

<400> SEQUENCE: 1

Glu Asp Trp Leu Thr Phe Gln Lys Lys His Ile Thr Asn Thr Arg Asp
   1               5                   10                  15

Val Asp Cys Asp Asn Ile Met Ser Thr Asn Leu Phe His Cys Lys Asp
                   20                  25                  30

Lys Asn Thr Phe Ile Tyr Ser Arg Pro Glu Pro Val Lys Ala Ile Cys
               35                  40                  45

Lys Gly Ile Ile Ala Ser Lys Asn Val Leu Thr Thr Ser Glu Phe Tyr
           50                  55                  60

Leu Ser Asp Cys Asn Val Thr Ser Arg Pro Cys Lys Tyr Lys Leu Lys
   65                  70                  75                  80

Lys Ser Thr Asn Lys Phe Cys Val Thr Cys Glu Asn Gln Ala Pro Val
                   85                  90                  95

His Phe Val Gly Val Gly Ser Cys
               100

<210> SEQ ID NO 2
   <211> LENGTH: 104
   <212> TYPE: PRT
   <213> ORGANISM: artificial
   <220> FEATURE:
   <223> OTHER INFORMATION: variant '805 of ranpirnase

<400> SEQUENCE: 2

Glu Asp Trp Leu Thr Phe Gln Lys Lys His Val Thr Asn Thr Arg Asp
   1               5                   10                  15

Val Asp Cys Asn Asn Ile Met Ser Thr Asn Leu Phe His Cys Lys Asp
                   20                  25                  30

Lys Asn Thr Phe Ile Tyr Ser Arg Pro Glu Pro Val Lys Ala Ile Cys
               35                  40                  45

Lys Gly Ile Ile Ala Ser Lys Asn Val Leu Thr Thr Ser Glu Phe Tyr
           50                  55                  60

Leu Ser Asp Cys Asn Val Thr Ser Arg Pro Cys Lys Tyr Lys Leu Lys
   65                  70                  75                  80

Lys Ser Thr Asn Lys Phe Cys Val Thr Cys Glu Asn Gln Ala Pro Val
                   85                  90                  95
```

```
His Phe Val Gly Val Gly Arg Cys
            100

<210> SEQ ID NO 3
<211> LENGTH: 114
<212> TYPE: PRT
<213> ORGANISM: Rana pipiens

<400> SEQUENCE: 3

Lys Pro Lys Glu Asp Arg Glu Trp Glu Lys Phe Lys Thr Lys His Ile
1               5                   10                  15

Thr Ser Gln Ser Val Ala Asp Phe Asn Cys Asn Arg Thr Met Asn Asp
            20                  25                  30

Pro Ala Tyr Thr Pro Asp Gly Gln Cys Lys Pro Ile Asn Thr Phe Ile
        35                  40                  45

His Ser Thr Thr Gly Pro Val Lys Glu Ile Cys Arg Arg Ala Thr Gly
    50                  55                  60

Arg Val Asn Lys Ser Ser Thr Gln Gln Phe Thr Leu Thr Thr Cys Lys
65                  70                  75                  80

Asn Pro Ile Arg Cys Lys Tyr Ser Gln Ser Asn Thr Thr Asn Phe Ile
                85                  90                  95

Cys Ile Thr Cys Arg Asp Asn Tyr Pro Val His Phe Val Lys Thr Gly
            100                 105                 110

Lys Cys

<210> SEQ ID NO 4
<211> LENGTH: 115
<212> TYPE: PRT
<213> ORGANISM: artificial
<220> FEATURE:
<223> OTHER INFORMATION: rAmphinase 2

<400> SEQUENCE: 4

Met Lys Pro Lys Glu Asp Arg Glu Trp Glu Lys Phe Lys Thr Lys His
1               5                   10                  15

Ile Thr Ser Gln Ser Val Ala Asp Phe Asn Cys Asn Arg Thr Met Asn
            20                  25                  30

Asp Pro Ala Tyr Thr Pro Asp Gly Gln Cys Lys Pro Ile Asn Thr Phe
        35                  40                  45

Ile His Ser Thr Thr Gly Pro Val Lys Glu Ile Cys Arg Arg Ala Thr
    50                  55                  60

Gly Arg Val Asn Lys Ser Ser Thr Gln Gln Phe Thr Leu Thr Thr Cys
65                  70                  75                  80

Lys Asn Pro Ile Arg Cys Lys Tyr Ser Gln Ser Asn Thr Thr Asn Phe
                85                  90                  95

Ile Cys Ile Thr Cys Arg Asp Asn Tyr Pro Val His Phe Val Lys Thr
            100                 105                 110

Gly Lys Cys
        115
```